(12) United States Patent
Hwang et al.

(10) Patent No.: US 8,475,339 B2
(45) Date of Patent: Jul. 2, 2013

(54) APPARATUS AND METHOD FOR CORRECTING LIFE PATTERNS IN REAL TIME

(75) Inventors: Jin-Sang Hwang, Suwon-si (KR); Young-Tae Im, Yongin-si (KR); Jeong-Whan Lee, Chungju-si (KR); Young-Jae Lee, Hanam-si (KR)

(73) Assignee: Xiusolution Co., Ltd., Yonging-Si (KR)

( * ) Notice: Subject to any disclaimer, the term of this patent is extended or adjusted under 35 U.S.C. 154(b) by 938 days.

(21) Appl. No.: 12/525,182

(22) PCT Filed: Feb. 4, 2009

(86) PCT No.: PCT/KR2009/000537
§ 371 (c)(1),
(2), (4) Date: Jul. 30, 2009

(87) PCT Pub. No.: WO2009/099292
PCT Pub. Date: Aug. 13, 2009

(65) Prior Publication Data
US 2010/0075807 A1    Mar. 25, 2010

(30) Foreign Application Priority Data

Feb. 4, 2008 (KR) .................. 10-2008-0011270
Aug. 19, 2008 (KR) .................. 10-2008-0080779
Jan. 14, 2009 (KR) .................. 20-2009-0000463

(51) Int. Cl.
*A63B 24/00*    (2006.01)

(52) U.S. Cl.
USPC .................. 482/8; 482/1; 482/9; 482/901

(58) Field of Classification Search
USPC .................. 482/1–9, 900–902; 434/247
See application file for complete search history.

(56) References Cited

U.S. PATENT DOCUMENTS

| | | | | |
|---|---|---|---|---|
| 5,469,740 A | * | 11/1995 | French et al. | 73/379.04 |
| 5,478,295 A | * | 12/1995 | Fracchia | 482/7 |
| 6,436,058 B1 | * | 8/2002 | Krahner et al. | 600/587 |
| 6,786,848 B2 | * | 9/2004 | Yamashita et al. | 482/8 |
| 7,416,537 B1 | * | 8/2008 | Stark et al. | 602/16 |

* cited by examiner

*Primary Examiner* — Glenn Richman
(74) *Attorney, Agent, or Firm* — Staas & Halsey LLP

(57) ABSTRACT

A method for correcting life patterns for providing feedback for an exercise program periodically or in real time is disclosed. The method of the present invention detects a starting point of a dynamic activity interval periodically or in real time by sensing movement of a user in daily life, and provides an exercise program for filling a deficient amount of activity compared to a target value in the detected activity interval when the starting point is detected. Therefore, the method of the present invention may simply provide feedback for an amount of activity of a pertinent interval at an actual starting point of the dynamic activity interval, and thus the user may effectively follow the provided exercise program for correcting life patterns.

12 Claims, 19 Drawing Sheets

FIG. 8

| ACTIVITY INTERVAL | DIFFERENCE VALUE | EXERCISE PROGRAM | TYPE |
|---|---|---|---|
| WORKING INTERVAL IN OFFICE | .... | .... | .... |
| MOVING INTERVAL FOR LEAVING OFFICE | 0 | DOING WELL IT'S OK TO GO HOME BY CAR | TEXT/ VOICE/IMAGE |
| | -50 | PLEASE GO HOME BY CAR, AND DO 5 LAPS AROUND THE YARD BEFORE YOU SLEEP | TEXT/ VOICE/IMAGE |
| | -100 | PLEASE GO HOME BY BUS YOU SHOULD STAND IN THE BUS | TEXT/ VOICE/IMAGE |
| | -150 | PLEASE GO HOME BY SUBWAY AND USE STAIRS INSTEAD OF ESCALATOR | TEXT/ VOICE/IMAGE |
| | -200 | PLEASE GET OFF SUBWAY ONE STOP BEFORE THE DESTINATION AND GO HOME BY FAST WALKING | TEXT/VOICE/ IMAGE/ VIBRATIONAL ALERT |
| REST INTERVAL AT HOME | .... | .... | .... |

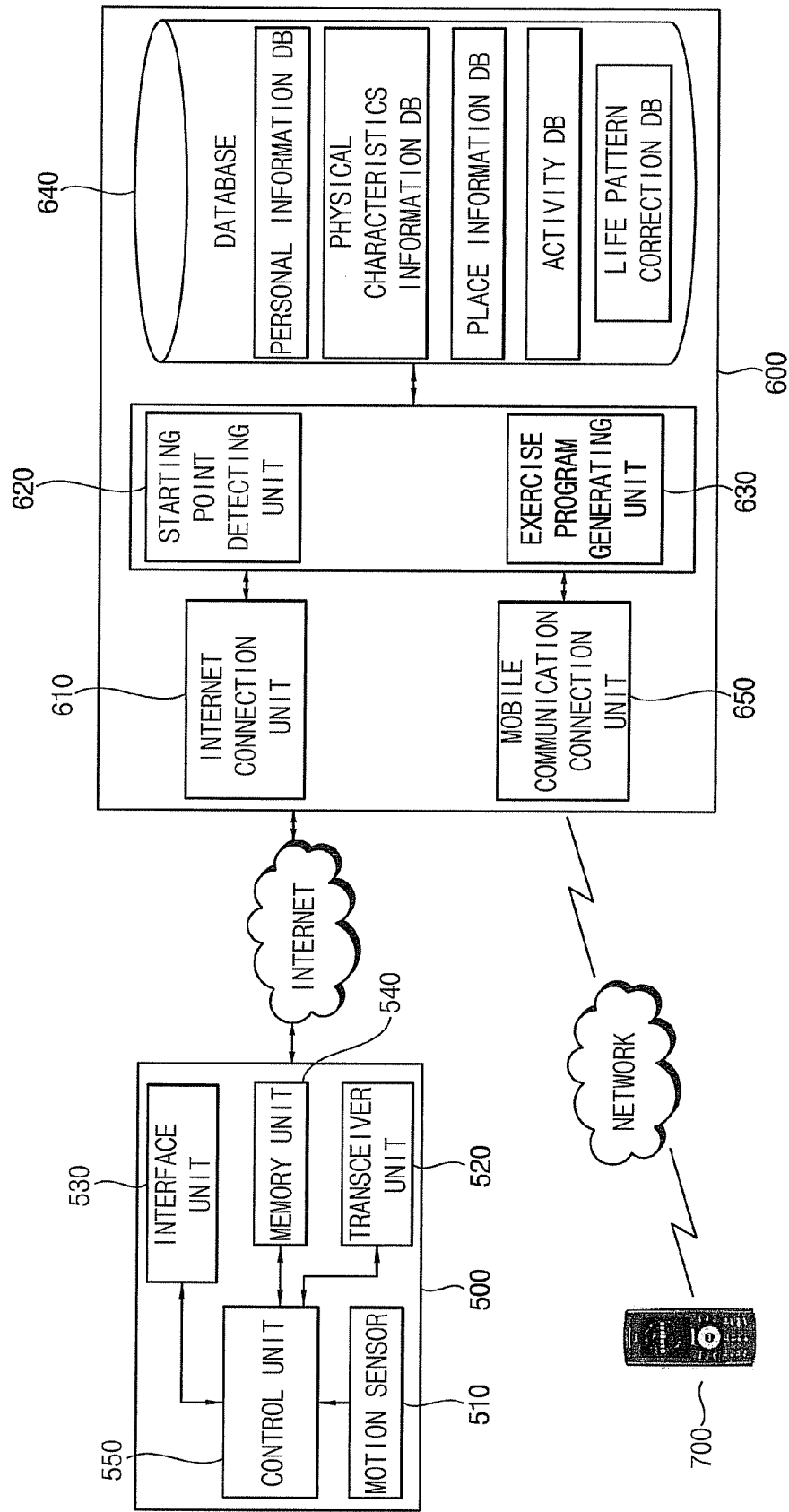

APPARATUS AND METHOD FOR CORRECTING LIFE PATTERNS IN REAL TIME

CROSS REFERENCE TO RELATED PATENT APPLICATIONS

This application claims the benefit under 35 U.S.C. Section 371, of PCT International Application No. PCT/KR2009/000537, filed Feb. 4, 2009, which claimed priority to Korean Patent Application No. 10-2008-0011270, filed Feb. 4, 2008, Korean Patent Application No. 10-2008-0080779, filed Aug. 19, 2008, and Korean Patent Application No. 20-2009-0000463, filed Jan. 14, 2009 in the Korean Intellectual Property Office, the disclosures of which are hereby incorporated by reference.

TECHNICAL FIELD

The present invention relates to an apparatus and a method for correcting life patterns, and more particularly to an apparatus and a method for correcting life patterns in which feedback of an amount of activity is provided at a starting point of a dynamic activity interval of a user periodically or in real time.

BACKGROUND ART

As the average human life span increases, public interest in health inevitably increases. Until now, the increase in the human life span has been due to the development of medical technology, and nowadays attempts to increase the human life span have been continually progressing by means of exercise and dietary habits. However, people may not be able to sufficiently exercise due to a complicated social structure, and thus an individual-specific health care system has been developed.

A conventional health care system requires a lot of information which contains private data, medical examination results, food intake status, caloric intake, physical fitness measurements, biological signals, daily amount of activity, caloric consumption, and so on. Furthermore, the conventional health care system gathers the information using expensive equipment. Users may be reluctant to input the information because the conventional health care system requires the users to input a lot of information, and thus the users may have difficulties in using the conventional health care system. Moreover, the conventional health care system cannot provide feedback when the information is not inputted by the users. As the system is implemented with various components, the cost of the components make the system too expensive to be widely used and the size of the components make the system too big to be carried by the users. Consequently, the conventional health care system may not correctly or consistently receive the required data, and thus correct health care may not be basically possible even though an analyzing system is excellent. The conventional health care system has some limitations such as being inconvenient to use, implementing size and costs.

A system and method for providing health information by using bodily information is disclosed in Korean Patent No. 0431923. It discloses that the system and method provide "a plurality of suitable diet information for each user by comprehensively evaluating bodily information and life patterns." However, the life patterns are not clearly defined in the specification and only an exercise prescription corresponding to the diet information is provided based on the bodily information received from the user. Finally, the system and method provide the diet information exclusively based on the bodily information received from the user, and thus the system and method may not provide appropriate exercise prescriptions when the user does not input the bodily information.

A system and method considering life patterns of a user is disclosed in Korean Patent No. 0682900. The user may have difficulties inputting their own life patterns and periods for providing health management feedback information are not clearly mentioned. Therefore, the health management feedback information is only provided on a daily basis, and the information may not be provided at a point in time when the user is able to exercise. The system and method may not increase the amount of activity, and thus a goal of health management considering life patterns may not be effectively accomplished.

The conventional method and apparatus require the input of excessive amounts of health-related data that make them inconvenient to use, and in cases where this is substituted with an automatic input means, the product price increases due to expensive sensor components and additional related software. Even though the information is automatically acquired, the health care information is not provided in real time but is checked afterward. Therefore, the adaptability of the user in following an actual life-pattern correction program may be lowered.

The conventional method and apparatus determines signal strengths generated by motion sensors under conditions in which sensing periods are fixed, classifies various activities such as dynamic, very dynamic, and static, or divides activity patterns during the fixed periods by using a certain algorithm. For example, a pedometer manufactured by Omron and linked software for a personal computer may divide the activity patterns per hour to provide feedback to the user. However, the user may not be able to obtain any substantial meaning from the feedback data. For instance, the user may view the provided life patterns as patterns that they already know, because the activity level is estimated to be at a high level only during the morning commute, movement during lunchtime, and the evening commute. Further processes like data mining the data collected remotely, or providing feedback that is realistic enough to change life patterns even though the health manager directly looks at the provided data are beyond its ability.

In addition, Body Media simply provides sensed life patterns per minute during 24 hours, and does not provide a detailed method for providing effective feedback by applying the sensed life patterns. Although respective activity patterns (events) may be stored to provide specified feedback to the user by analyzing the sensed data, the amount of the data is too great to be analyzed by only one measuring apparatus and the apparatus may be expensive to be implemented. Further, a traffic may be increased by continually transferring the excessive data to a server, and the server collecting all of the data and analyzing trends may be burdened in maintaining and managing the received database.

DISCLOSURE OF THE INVENTION

Technical Problem

The present invention provides an apparatus and a method of correcting life patterns with excellent correction effect by periodically or in real time analyzing the activity state of a user and providing exercise programs for a pertinent activity interval at a starting point of a dynamic activity interval such that the exercise programs may be immediately implemented by the user.

The present invention provides an apparatus and a method of correcting life patterns improving convenience of use by minimizing required information.

The present invention provides an apparatus and a method of correcting life patterns providing an adaptive exercise program considering the daily life patterns of the user with a simple structure for sensing movement of the user such that implementation costs may be reduced.

The present invention provides an apparatus and a method of correcting life patterns providing an improved correction effect by shortening a determined period of activity patterns in a dynamic activity interval, compared to other intervals. The dynamic activity interval requires more adaptive feedback for providing an exercise program of a pertinent activity interval at a starting point thereof by analyzing the activity state of the user periodically or in real time.

The present invention provides an apparatus and a method of correcting life patterns accurately and correctly estimating activity intensities by accurately classifying the life patterns of the user.

Technical Solution

To accomplish the goal mentioned above, a method according to an example embodiment of the present invention senses movement of a user in daily life, detects a starting point of a dynamic activity interval periodically or in real time, and provides an exercise program of a pertinent activity interval for filling a deficient or lacking amount of activity compared to a target value when the starting point is detected.

In detecting the starting point, a corresponding event is generated by a sensor which senses the movement of the user, a unit activity pattern per unit time is determined based on the generated event, consumed calories corresponding to the unit activity pattern is accumulated to produce an accumulated value, a difference value is calculated by comparing the accumulated value and the target value, and one of observation intervals in which the movement of the user rapidly changes as the starting point by comparing average amounts of activity of the observation intervals.

In selecting the unit activity pattern, an event which has the greatest consumed calories may be selected in response to a ratio of each event per unit time, and the selected event may be determined as the unit activity pattern.

The unit time may be 1 minute, and the unit activity pattern may be an ordinary life activity which may include at least one of resting, slow walking, walking, fast walking, running and going up stairs.

The observation interval may be 5 to 10 minutes.

The exercise program according to the present invention may be provided by at least one of text, voice, light and vibrations.

In detecting the starting point, a corresponding exercise program may be provided when the detected starting point is within an error range of a starting time of the activity interval included in a daily schedule with reference to the daily schedule of the user. When the detected starting point deviates from the error range, the user may be warned that the life pattern is deviating from a regular life pattern.

Alternatively, a corresponding exercise program may be provided at the detected starting point of which the amount of activity rapidly increases.

In a method for correcting life patterns in real time according to some example embodiments, activity information is generated in real time based on movement of a user, the generated information is stored in real time, the stored activity information is transmitted to a server using a network, starting point information of a dynamic activity interval and an exercise program is received from the server, and the exercise program is provided to the user.

In a method for correcting life patterns in real time according to some example embodiments, activity information based on movement of a user who possesses a handheld terminal is periodically received, a starting point of a dynamic activity interval of the user is detected based on the received activity information, an exercise program for filling a deficient amount of activity compared to a target value in the detected dynamic activity interval is generated, and the generated starting point information and the exercise program information are transmitted to the handheld terminal.

In a method for correcting life patterns in real time according to some example embodiments, activity information is generated by a mobile device based on movement of a user in real time, the generated activity information is stored, the stored activity information is periodically transmitted to a server using a network, a starting point of a dynamic activity interval is detected based on the transmitted activity information from the mobile device, an exercise program for filling a deficient amount of activity compared to a target value in the detected dynamic amount of activity is generated when the starting point is detected, and the generated exercise program is transmitted to a mobile device using a short message service (SMS) when a time of another day corresponds to the detected starting point of the day.

An apparatus for correcting life patterns implemented as a stand-alone type includes a movement sensing unit, a starting point detecting unit, an exercise program generating unit, and a user interface unit. The movement sensing unit senses movement of a user in daily life. The starting point detecting unit detects a starting point of a dynamic activity interval based on the sensed activity information periodically or in real time. The exercise program generating unit generates an exercise program for filling a deficient amount of activity compared to a target value in the detected dynamic activity interval when the starting point is detected. The user interface unit provides the generated exercise program to the user. For example, the starting point detecting unit may include an event generating module, a unit activity pattern, an accumulating module, a calculating module, and a detecting module. The event generating module may generate a corresponding event in response to the sensing signal from the movement sensing unit. The unit activity pattern determines a unit activity pattern per unit time based on the generated event. The accumulating module accumulates consumed calories corresponding to the unit activity pattern. The calculating module calculates a difference value between the accumulation value and the target value. The detecting module compares an average amount of activity for every observation interval based on the determined unit activity pattern to detect the starting point in which the amount of activity rapidly changes.

An apparatus according to another example embodiment includes a movement sensing unit, a starting point detecting unit, an exercise program generating unit, and a user interface unit. The movement sensing unit senses movement of a user in daily life. The starting point detecting unit detects a starting point of a dynamic activity interval for a first activity pattern determination period, and sets an activity pattern determination period as a second activity pattern determination period during activity intervals in which the starting point is detected. The second activity pattern determination period is different from the first activity pattern determination period.

The exercise program generating unit generates an exercise program for filling a deficient amount of activity compared to a target value in the detected dynamic activity interval. The user interface unit provides the generated exercise program to the user.

The starting point detecting unit may include an event generating module, a determining module, a determination period selecting module, an accumulating module, a calculating module, and a detecting module. The event generating module may generate a corresponding event in response to the sensing signal sensed by the movement sensing unit. The determining module may determine a representative activity pattern for a first activity pattern determination period based on the generated event. The determination period selecting module may set the second activity pattern determination period during the activity intervals where the starting point is detected, and provide the set determination period to the determining module. The second activity pattern determination period is different from the first activity pattern determination period. The accumulating module may accumulate consumed calories corresponding to the representative activity pattern to produce an accumulated value. The calculating module may calculate a difference value by comparing the accumulated value and the target value. The detecting module may compare average amounts of activity for an observation period to detect the starting point at which the amount of activity rapidly changes.

The present invention may be implemented as an online system including a handheld terminal and a server.

In the handheld terminal, activity information is generated periodically or in real time based on movement of a user, the generated activity information is transmitted to the server through a network, starting point information of a dynamic activity interval and exercise program information are received from the server, and the exercise program information is provided at the starting point of the received dynamic activity interval.

In the server, the activity information generated based on the movement of the user who possesses the handheld terminal is received periodically or in real time, the starting point of the dynamic activity interval is detected based on the received activity information, the exercise program for filling a deficient amount of activity compared to a target value is generated when the starting point is detected, and the generated starting point information and the exercise program information are transmitted to the handheld terminal.

A handheld terminal according to the present invention includes a movement sensing unit, a transceiver unit, a user interface unit, and a control unit. The movement sensing unit generates activity information based on movement of a user in real time. The transceiver unit transmits the generated activity information through a network, and receives starting point information and an exercise program of a dynamic activity interval from a server. The control unit outputs an exercise message corresponding to the exercise program information at the starting point of the received dynamic activity interval through the interface unit.

A server according to the present invention includes a transceiver unit, a starting point detecting unit, and an exercise program generating unit. The transceiver unit receives activity information generated based on movement of a user, and transmits generated starting point information and exercise program information to the handheld terminal. The starting point detecting unit detects a starting point of a dynamic activity interval based on the received activity interval information. The exercise program generating unit generates an exercise program for filling a deficient amount of activity compared to a target value in the detected dynamic activity interval when the starting point is detected.

Advantageous Effects

An adaptive apparatus for correcting life patterns according to the present invention may improve adaptability of a user by minimizing inconvenience caused by inputting information, may provide an effective life pattern correction service by providing feedback at a time when the user may be able to act in real time, and may be implemented at low cost to be widely spread.

An adaptive method of correcting life patterns may provide an effective life pattern correction service at a time when the user may be able to act in real time by using little information.

In addition, an apparatus for correcting life patterns may shorten an activity pattern determination period when life patterns of the user are variously changed, or the user or a health manager is required to make an intensive analysis, and thus the life patterns of the user may be accurately sensed. Otherwise, the activity pattern determining period may be lengthened to reduce unnecessary data so that the apparatus and systems may be implemented in a smaller form.

Moreover, because an apparatus for correcting life patterns adapts an activity level to non-standardized activity patterns, the apparatus may adaptively provide feedback based on the accurately calculated calories, and thus the life patterns may be effectively corrected.

BRIEF DESCRIPTION OF THE DRAWINGS

FIG. 8 is a lookup table of an exercise program generated by an exercise program generating unit.

in FIG. 5.

FIG. 20 is a block diagram illustrating an example of online server supported system for correcting life patterns according to the present invention.

Hereinafter, embodiments according to the present invention will be described more fully with reference to the accompanying drawings. These embodiments are provided so that this disclosure will be thorough and complete, and will fully convey the scope of the invention to those skilled in the art.

BEST MODE FOR CARRYING OUT THE INVENTION

Hereinafter, embodiments according to the present invention will be described more fully with reference to the accompanying drawings. These embodiments are provided so that this disclosure will be thorough and complete, and will fully convey the scope of the invention to those skilled in the art.

1. Example Embodiment 1

Stand-Alone Type

The present invention may be implemented in a stand-alone apparatus having a portable size. For example, the stand-alone apparatus may be implemented by combining an electronic pedometer, a portable electronic sphygmomanometer, an MP3 player, a portable multimedia player (PMP), a Digital Multimedia Broadcasting (DMB) receiver, a portable radio player, or a cellular phone, or may be independently implemented as a portable electrical device.

Figure 1:
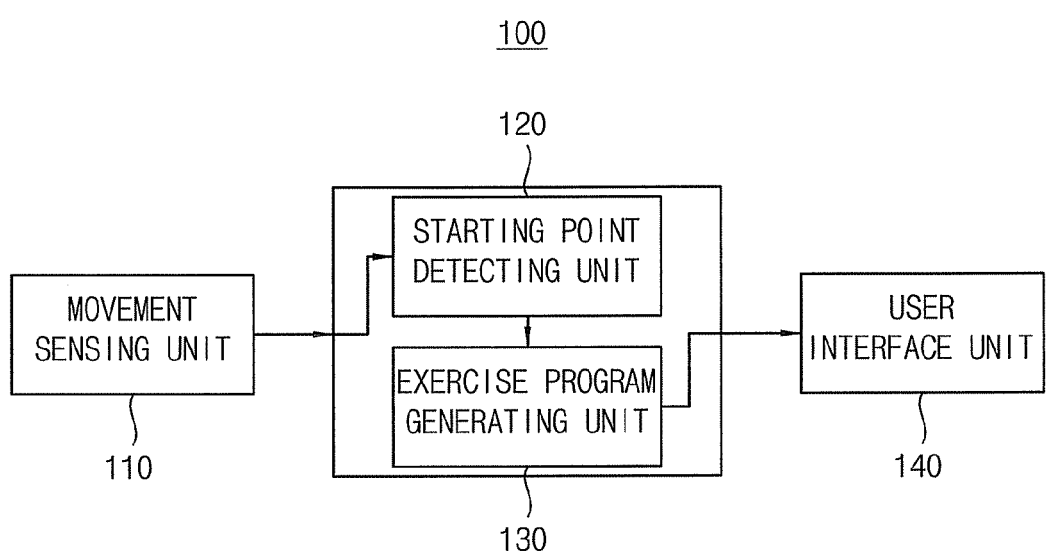
FIG. 1 is a block diagram illustrating a stand-alone apparatus for correcting life patterns according to the present invention.

FIG. 1 is a block diagram illustrating a stand-alone apparatus for correcting life patterns according to the present invention.

An apparatus for FIG. 1 may include a movement sensing unit 110, a starting point detecting unit 120, an exercise program generating unit 130, and a user interface unit 140.

The movement sensing unit 110 may be implemented with an inclination sensor, or a two- or three-axis acceleration sensor. The movement sensing unit 110 outputs sensing signals of the sensors as movement information in response to movements of a user. The movement sensing unit 110 may include a terrestrial magnetic sensor or angular velocity sensor for further accurate sensing of the movements.

The starting point detecting unit 120 detects a starting point of a dynamic activity interval periodically or in real time based on the sensed movement information. The exercise program generating unit 130 generates an exercise program of the detected activity interval for inducing the user to fill a deficient amount of activity compared to a target amount of activity when the starting point is detected. The starting point detecting unit 120 and the exercise program generating unit 130 may be implemented on an application-specific integrated circuit (ASIC) chip as hardware or as software by using a microprocessor or a microcomputer system.

The user interface unit 140 provides the generated movement information through visual sense (liquid crystal display (LCD) unit), auditory sense (speaker), and tactile sense (vibrator) to the user. The user interface unit 140 may further include an output means outputting feedback information as well as an input means such as a keyboard.

Figure 2:
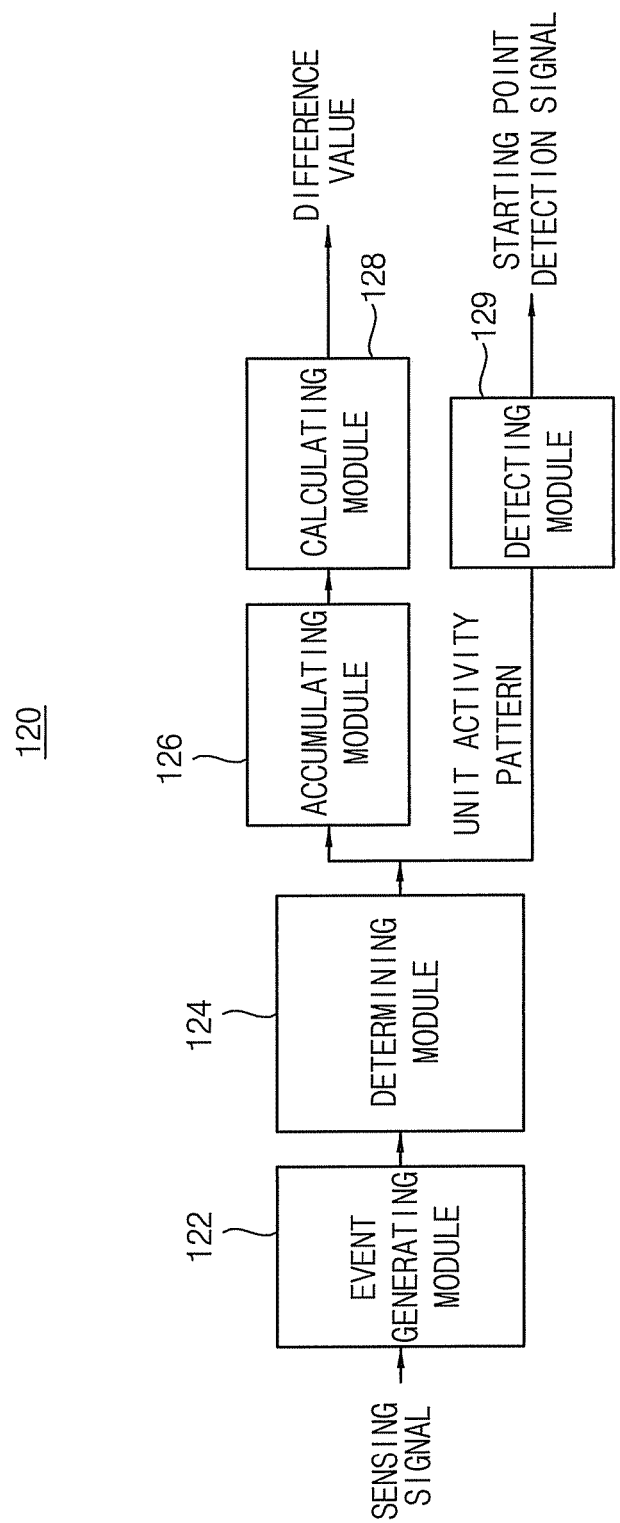
FIG. 2 is a detailed block diagram illustrating a preferred example embodiment of the starting point detecting unit 120 in FIG. 1.

FIG. 2 is a block diagram illustrating a preferred example embodiment of the starting point detecting unit 120 in FIG. 1.

Referring to FIG. 2, the starting point detecting unit 120 may include an event generating module 122, a determining module 124, an accumulating module 126, a calculating module 128, and a detecting module 129.

Figure 3:
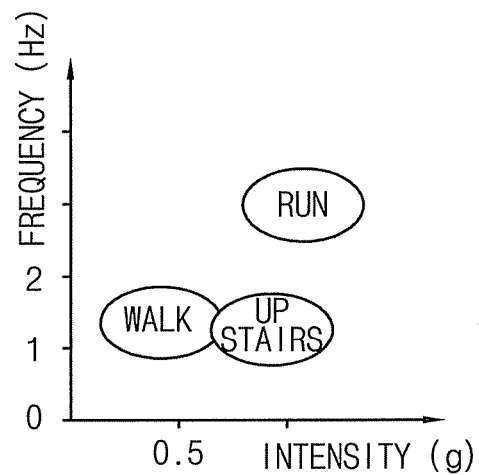
FIG. 3 illustrates activity patterns based on intensity relative to frequency of the gravity directional component of acceleration signals.
Figure 4:
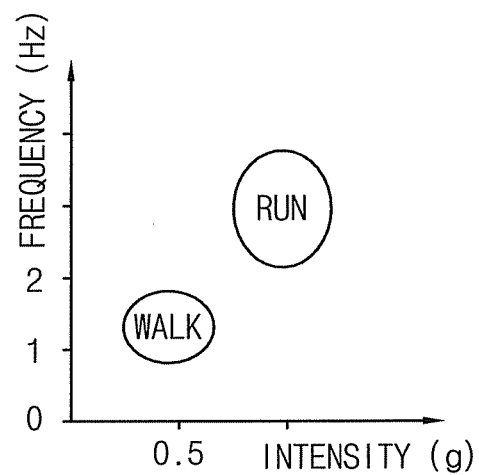
FIG. 4 illustrates activity patterns based on intensity relative to frequency of the horizontal directional component of the acceleration signals.

The event generating module 122 analyzes movement patterns, for example, slow walking, walking, fast walking, running, going up stairs, going down stairs, and so on by using a gravity directional component and a horizontal directional component of acceleration signal included in the sensing signals provided by the movement sensing unit 110, and generates events when the corresponding movement pattern is detected. FIG. 3 illustrates movement patterns based on intensity relative to frequency of the gravity directional component of the acceleration signals and FIG. 4 illustrates movement patterns based on intensity relative to frequency of the horizontal directional component of the acceleration signals. The determining method by analyzing the acceleration signals is substantially the same or similar to the method disclosed in the Korean Patent No. 601981 so that a precise description regarding the determining method of the present invention will be omitted.

Figure 5:
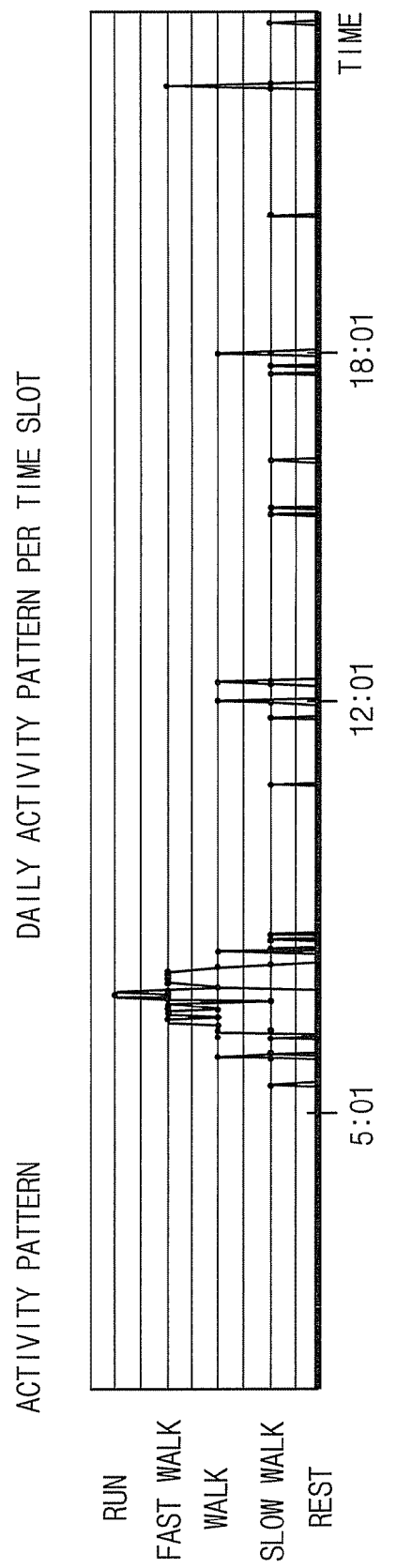
FIG. 5 illustrates an example of the determined daily representative activity patterns per time slot by the determining module 124 when the determination period is set to 1 minute.

The determining module 124 determines a representative movement pattern for every determination period based on the generated event. For example, events generated during the determination period may sort out each movement pattern event, and then the time of each of the sorted movement pattern events is accumulated and compared with each other. The event which has the greatest total time is determined as the representative movement pattern in the pertinent determination period. When another event which has the greatest total time exists, the movement pattern that has more consumption calories is determined as the representative movement pattern. For example, when an event corresponding to a walking movement pattern has the same total time compared to an event corresponding to a running movement pattern, the running movement pattern which has more consumed calories may be determined as the representative movement pattern. FIG. 5 illustrates an example of representative movement patterns determined by the determining module 124 according to a daily time slot when the determination period is set to 1 minute.

The accumulating module 126 accumulates consumed calories in real time with reference to a lookup table including the consumed calories corresponding to the determined representative movement pattern, for example, resting corresponds to 10 kcal, the slow walking corresponds to 50 kcal, the walking corresponds to 70 kcal, and the fast walking corresponds to 100 kcal, the running corresponds to 200 kcal, and generates the accumulated value.

Figure 6:
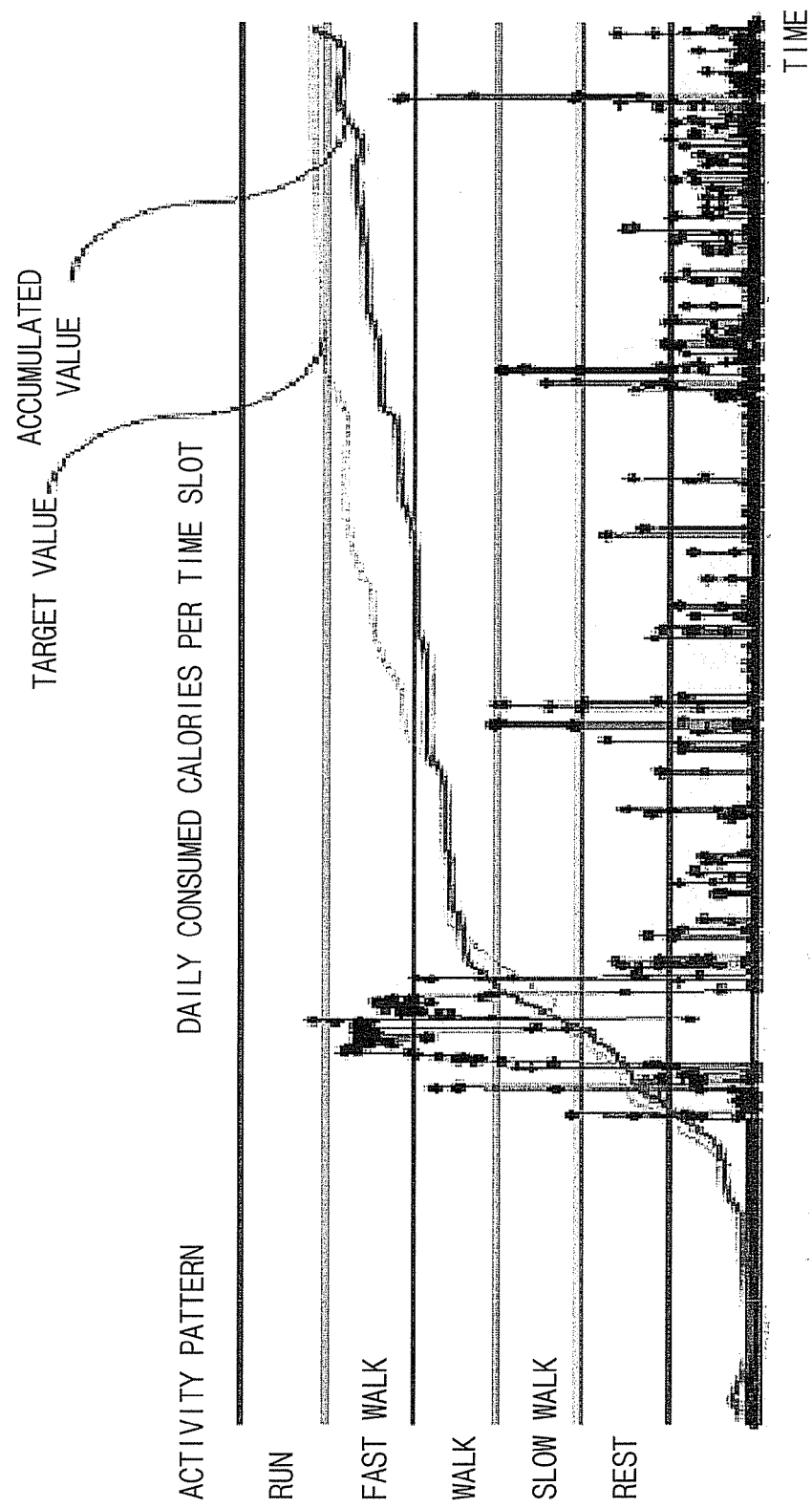
FIG. 6 is a graph illustrating each consumed calories (fine solid line), target calories (fine dotted line), and an accumulated calories (bold solid line).

FIG. 6 is a graph illustrating each consumed calories (fine solid line), target calories (fine dotted line), and an accumulated calories (bold solid line).

The calculating module 128 compares the accumulated value and the target value and calculates difference value between the accumulated value and the target value. A standardized exercise index may include a standard weight of the user and a recommended daily caloric consumption of the user. For example, when the user is a 40 year old male whose weight corresponds to 70 kg, the standard weight of the user is 66.24 kg and a body mass index is 10.57%, and thus the user falls under the overweight category. 2,856 kcal which contains an additional 70% of a basal metabolic rate may correspond to the recommended daily caloric consumption of the user. Referring to the consumed calories according to the daily time slot, daily consumed calories by exercise is estimated as 565 kcal, and thus the daily target consumed calories correspond to 611 kcal obtained by substituting the basal metabolic rate of 1,680 kcal from the recommended daily caloric consumption.

The detecting module 129 accumulates the amount of activity in observation intervals based on the determined representative movement patterns, for example, resting is 1, slow walking is 2, walking is 3, fast walking is 4, and running is 5, is weighted and averaged, and then the average values in the observation interval are compared so that one of the observation intervals in which the amount of activity rapidly changes is detected as the starting point or an ending point. When the amount of activity rapidly changes and increases, the detected observation interval corresponds to the starting point. When the amount of activity rapidly changes and decreases, the detected observation interval corresponds to the ending point.

Figure 7:
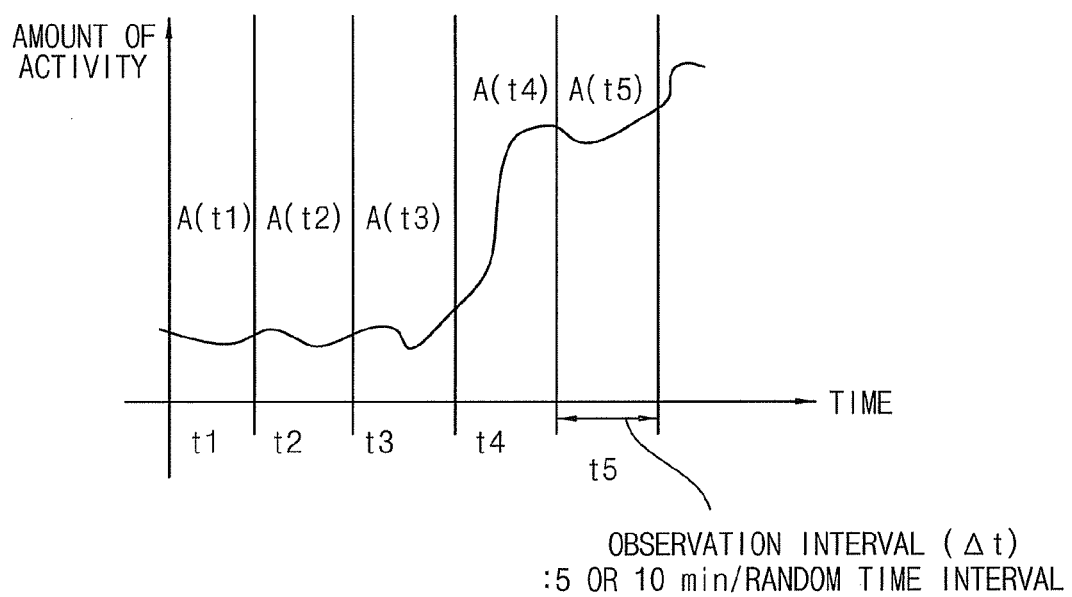
FIG. 7 is a diagram for describing a detection algorithm used in the detecting module 129.

FIG. 7 is a diagram for describing a detection algorithm used in the detecting module 129. Referring to FIG. 7, when the average amount of activity A(t4) in the observation interval t4 rapidly changes by greater than or equal to 150% compared to the average amount of activity A(t3) in the observation interval t3, the observation interval t4 is perceived as the starting point of the dynamic activity interval, such as a movement interval or an exercise interval. Otherwise, the average amount of activity at a present time is compared to average amounts of activity during a certain period such as one week, two weeks, or one month so that the starting point may be detected.

The exercise program generating module 130 provides a corresponding exercise program when the detected starting point is within a margin of error in a life activity interval of a daily activity schedule with reference to the daily activity schedule of the user. Alternatively, the exercise program generating module 130 warns that the user is deviating from regular life patterns when the detected starting point is not within a margin of error. The exercise program generating module 130 generates the exercise program including a life pattern correction message corresponding to a difference value of the consumed value and the target value through at least one of voice, text, images and vibrations with reference to a lookup table of FIG. 8 in response to the detected starting point. For instance, the message "Please take a subway to go home because you lack 200 kcal compared to the target consumed calories at the present time of 6:00 p.m. corresponding to a leaving office interval," may be provided to the user as the exercise program.

Figure 9:
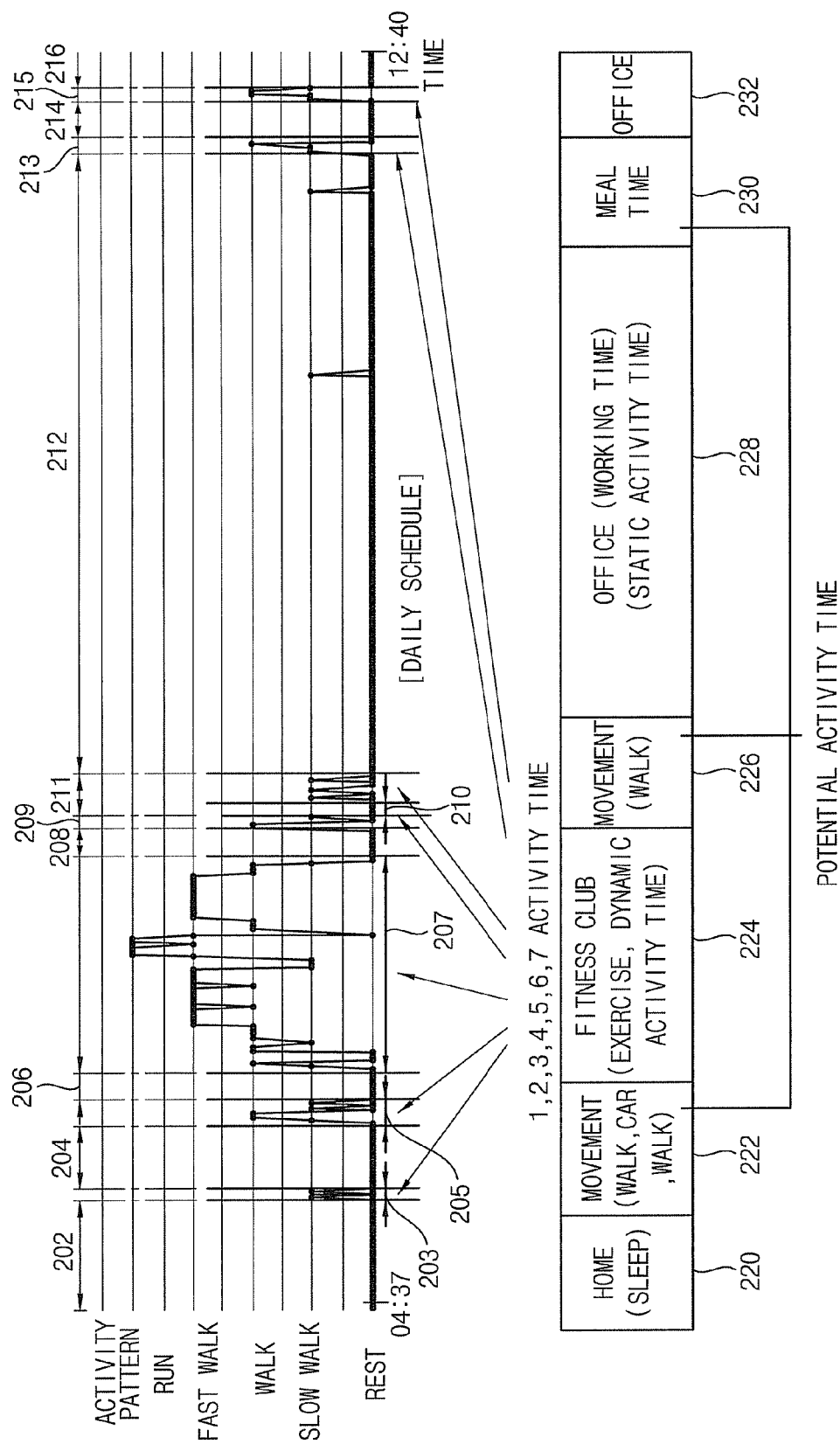
FIG. 9 is a diagram illustrating an activity interval and a daily schedule from 4:37 a.m. to 12:40 a.m.

FIG. 9 is a diagram illustrating an activity interval and a daily schedule from 4:37 a.m. to 12:40 a.m. in FIG. 5. The activity intervals of the user may be determined according to a duration time of the activity state and an accumulation value of the consumed calories. For example, the dynamic activity interval may be determined when the activity state is slow walking that continues for 5 or more minutes, or a continuous accumulated value of the consumed calories is greater than or equal to a certain value. The duration time and the accumulation value of the consumed calories may be differently defined according to the personal information.

Referring to FIG. 9, the user has a total of seven dynamic activity intervals 203, 205, 207, 209, 211, 213, and 215 and eight static activity intervals 202, 204, 206, 208, 210, 212, 214, and 216. When the user inputs activity places including a home, an office and a fitness club, a plurality of intervals is determined. Whether an interval is an activity interval of the activity places or a movement interval between the activity intervals is determined, based on the duration times of the activity intervals and intervals between the activity intervals. An interval between the activity intervals may be defined as a time difference between an ending point of a first activity interval and a starting point of a second activity interval. An interval before an activity starts in the morning 202 is determined as an activity interval in the home 220, an interval in which a fast walking state is maintained for a long time 207 is determined as an activity interval in the fitness club 224, and an interval in which a static state is maintained for a long time 212 is determined as an activity interval in the office 228 and 232. Other intervals are determined as the movement intervals 222, 226, and 230 between the activity places.

The user interface unit 140 may receive information including transportation between the activity places as well as a duration of stay at the activity places according to preferences of the user.

When durations of stay are not inputted by the user, the activity intervals 206 and 208 are determined as the static activity intervals for traveling between the activity places. However, when the duration of stay at the fitness club is inputted by the user such that the duration of stay is between the activity intervals 206 and 208, the activity intervals 206 and 208 are determined as the static activity intervals in the activity places. Thus, when the duration of stay is inputted, the life patterns of the user may be precisely known so that the life patterns may be corrected during the static activity intervals for traveling between the activity places. Moreover, when the transportation for traveling are inputted, a preferred travel method may be provided to the user during the static activity interval for traveling.

With reference to FIG. 9, a total activity interval may correspond to an 8-hour observation interval from 4:31 a.m. to 12:31 a.m., in which the user needs to consume approximately 203 kcal which is about one-third of 611 kcal corresponding to the daily recommended consumed calories. The sum of the dynamic activity interval corresponds to 120 minutes, and then the user needs to consume approximately 136 kcal during the dynamic activity interval in the fitness club 207 that continues for about 80 minutes according to a time distribution. In addition, information for life pattern correction is generated especially based on characteristics of respective activity places, and thus the required consumed calories during the dynamic activity interval in the fitness club 207 may be more than 136 kcal. The activity interval 204 is determined as the static activity interval for traveling from home to the fitness club. The user may exercise but does not exercise in the static activity interval, so that the exercise program for correcting life patterns may be generated to consume calories.

Figure 10:
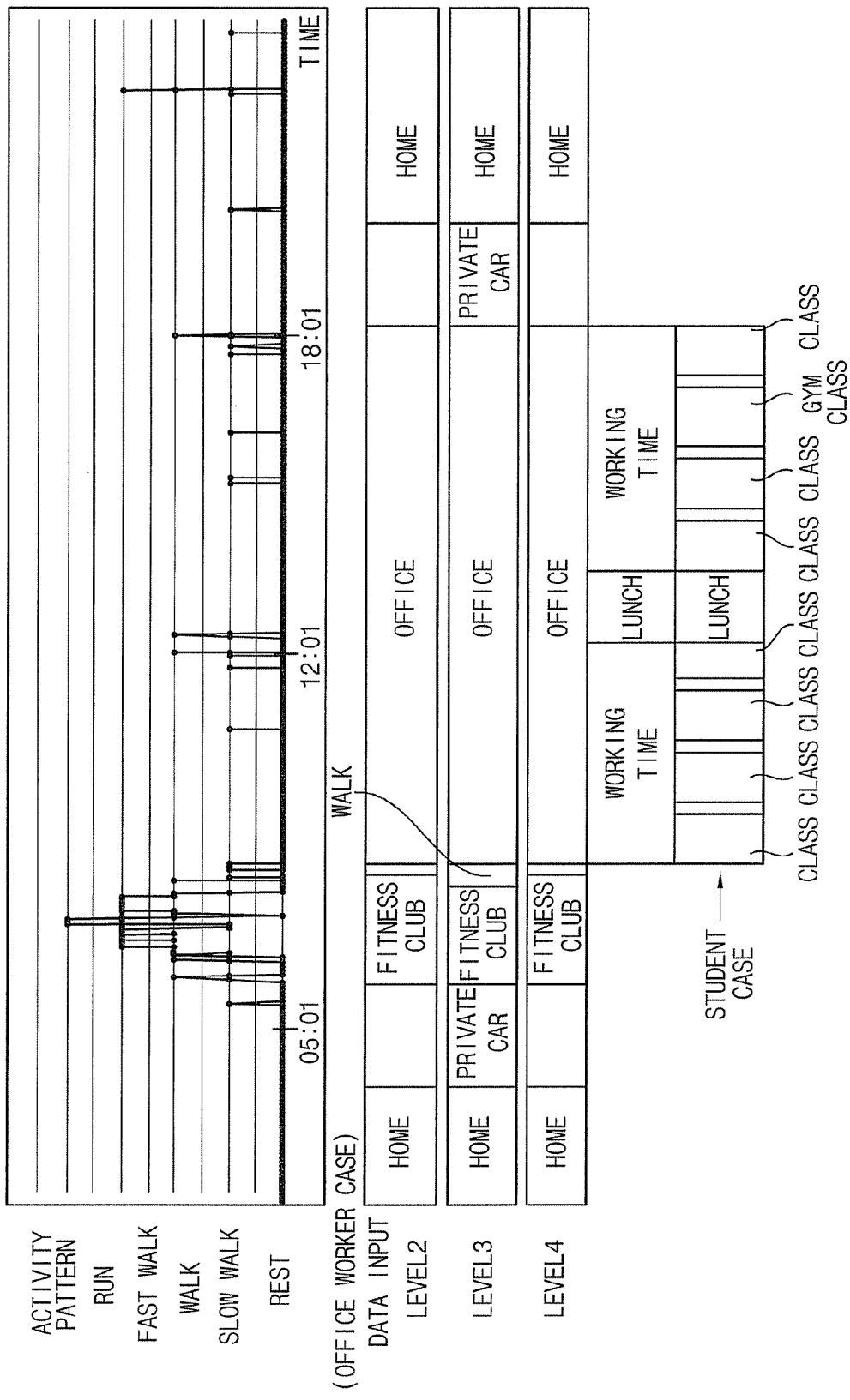
FIG. 10 illustrates daily schedules corresponding to activity intervals according to four stages.

FIG. 10 illustrates daily schedules corresponding to activity intervals according to four stages. Referring to FIG. 10, level 1 corresponds to a case where the user exclusively inputs the activity places, and levels 2 to 4 correspond to levels requiring more information for providing effective feedback to the user. The input of the activity places may be an effective solution without requiring additional functions, such as a global positioning system (GPS) and radio frequency identification (RFID).

Level 2 corresponds to a case where the user inputs the starting point and the ending point of the plurality of the activity places such as a first activity place corresponding to a user's present place of residence, a second activity place occupying a second major activity place in the daily schedule (i.e., an office for a office worker and a school for a student), and a third activity place (i.e., a fitness club). The activity intervals may be clearly divided by receiving the information of the duration of stay.

Level 3 corresponds to a case where the user inputs the transportation (i.e., a private car, public transportation such as a subway and bus) between the activity places. The information of the transportation may be used for calculating the amount of activity.

Level 4 corresponds to a case where the user inputs relative information of sub-activity intervals for each activity interval, and thus the amount of activity may be precisely calculated.

For correcting life patterns, it is preferable for both the static activity intervals for traveling between the activity places, as well as the dynamic activity intervals to be effectively used. Therefore, it is preferable for an exercise request to be made to the user may be provided at the starting point of the static activity interval for traveling between the activity places. The information for correcting life patterns may be provided to the user during the activity intervals for traveling between the activity places regardless of whether the activity interval corresponds to the static activity interval or the dynamic activity interval. When the user is the student, the apparatus may detect the activity state of the student during class, measure the concentration level of the student, and provide feedback regarding the conditions of the student for improving learning abilities.

Figure 11:
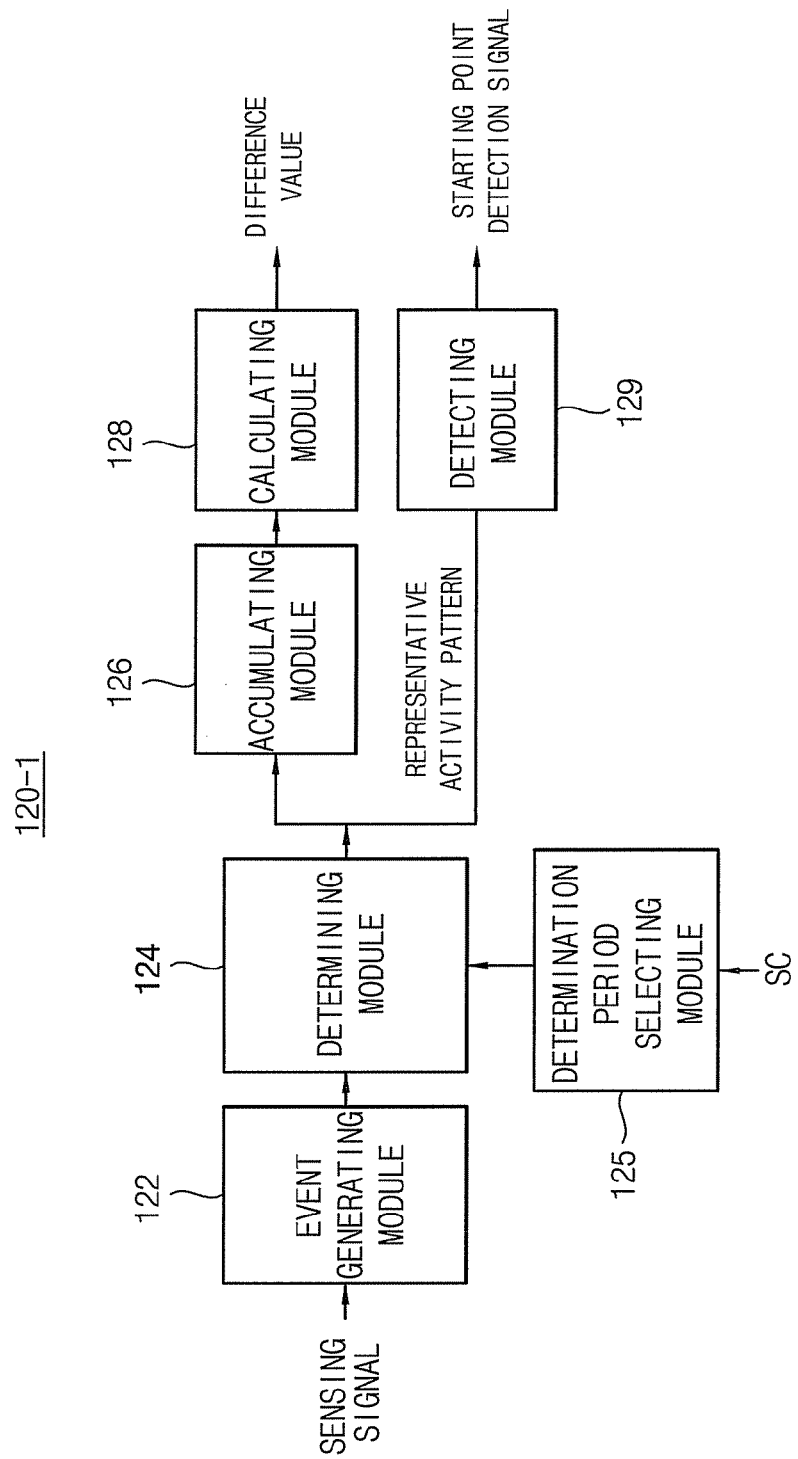
FIG. 11 is a detailed block diagram illustrating another preferred example of the starting point detecting unit 120 in FIG. 1.

FIG. 11 is a detailed block diagram illustrating another preferred example of the starting point detecting unit 120 in FIG. 1.

Another example of the starting point detecting unit 120-1 may further include a determination period selecting module 125 compared to the above-mentioned starting point detecting unit 120. The same parts of the starting point detecting unit 120-1 compared to the starting point detecting unit 120 in FIG. 1 are represented with the same reference numerals, so that a detailed description regarding the same parts will be omitted.

Figure 12:
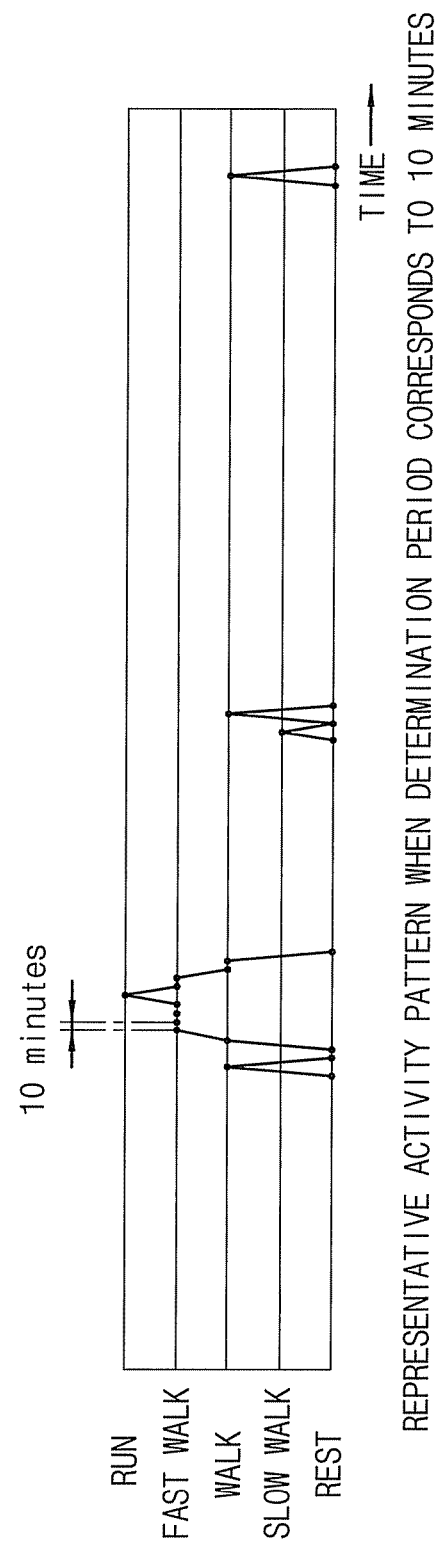
FIG. 12 illustrates an example of determined daily representative activity patterns per time slot by the determining module 124 when the determination period is set to 10 minutes.

FIG. 5 illustrates an example of the determined daily representative activity patterns per time slot by the determining module 124 when the determination period is set to 1 minute. FIG. 12 illustrates an example of determined daily representative activity patterns per time slot by the determining module 124 when the determination period is set to 10 minutes.

When the determination period is shortened, the representative activity patterns may be more precisely determined, and thus the amount of activity may be calculated more correctly. However, because of a large amount of data of the obtained representative activity patterns, a system may require sufficient storage space for storing the data. Alternatively, when the determination period is lengthened, the amount of data being processed may reduce a processing load in the system, but the amount of activity may be calculated with some errors. Therefore, system designers have no choice but to balance both accuracy and the system load.

The determination period selecting module 125 transfers a selected determined period to the determining module 124 in response to a selection control signal SC. For feedback, the determination period selecting module 125 may select a short determination period during the activity intervals that need to be precisely analyzed and select a long determination period during the activity interval that may be roughly analyzed. An optimal amount of activity may be calculated within appropriate system design specifications, so that the system may provide effective feedback. The selection control signal SC may be set through the user interface by the user or a health manager. The selection control signal SC may be automatically generated in response to the starting point detection signal. Generation of the starting point detection signal means that the activity interval corresponds to the dynamic activity interval in which the feedback is actively provided, and thus the determination period is controlled to be shortened. The determination period is controlled to be lengthened in remaining intervals excluding the dynamic activity intervals.

Figure 13:
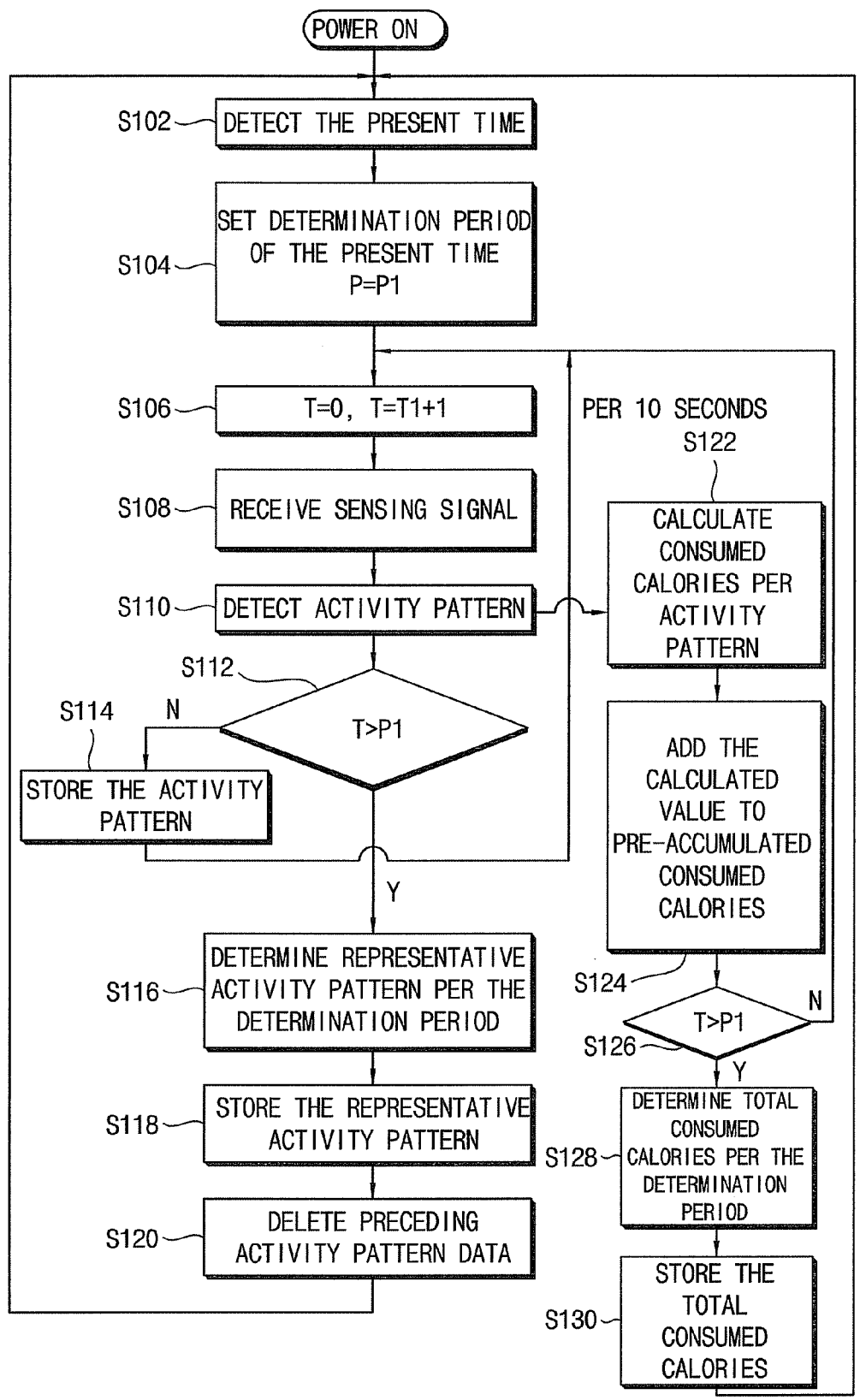
FIG. 13 is a flowchart illustrating a detecting program according to a preferred example where the user or the health manager inputs the determination period corresponding to the activity intervals.

FIG. 13 is a flowchart illustrating a detecting program according to a preferred example where the user or the health manager inputs the determination period corresponding to the activity intervals.

When power is on, the determination period selecting module 125 detects a present time (step S102), inputs the present time as the selection control signal SC, and selects the determination period P1 (step S104). When the present time corresponds to the dynamic activity interval requiring the feedback, the shortened determination period is selected. When the present time corresponds to the static activity interval such as the class, working time, or sleeping time, the lengthened determination period is selected.

The event generating module 122 sets a value of a parameter T to an initial value (step S106), obtains a sensing signal from the movement sensing unit 110 (step S108), determines the activity patterns, and generates the event (step S110). The determining module 124 compares the value of the parameter T and the determination period P1 (step S112). When the value of the parameter T is smaller than the determination period P1, the determining module 124 stores the determined activity patterns classified into each type of the activity patterns (step S114) and the detecting program returns to step S106. The detecting program increases the value of the parameter T, determines the activity patterns, and stores the determined activity patterns during the determination period.

In step S112, the representative activity pattern in the determination period P1 is determined when the value of the parameter T is greater than the determination period P1 (step S116). When the representative activity pattern is determined, the representative activity pattern is stored (step S118) and the preceding stored activity pattern data is deleted (step S120).

The accumulating module 126 calculates the consumed calories per activity pattern in step S110, and adds the consumed calories to the pre-accumulated consumed calories (step S124). The calculating module 128 compares the determination period and the value of the parameter T (step S126), determines total consumed calories after the value of the parameter T becomes greater than the determination period (step S128), and stores the consumed calories during the determination period (step S130).

Therefore, the representative activity pattern and the total consumed calories may be stored for each determination period.

Figure 14:
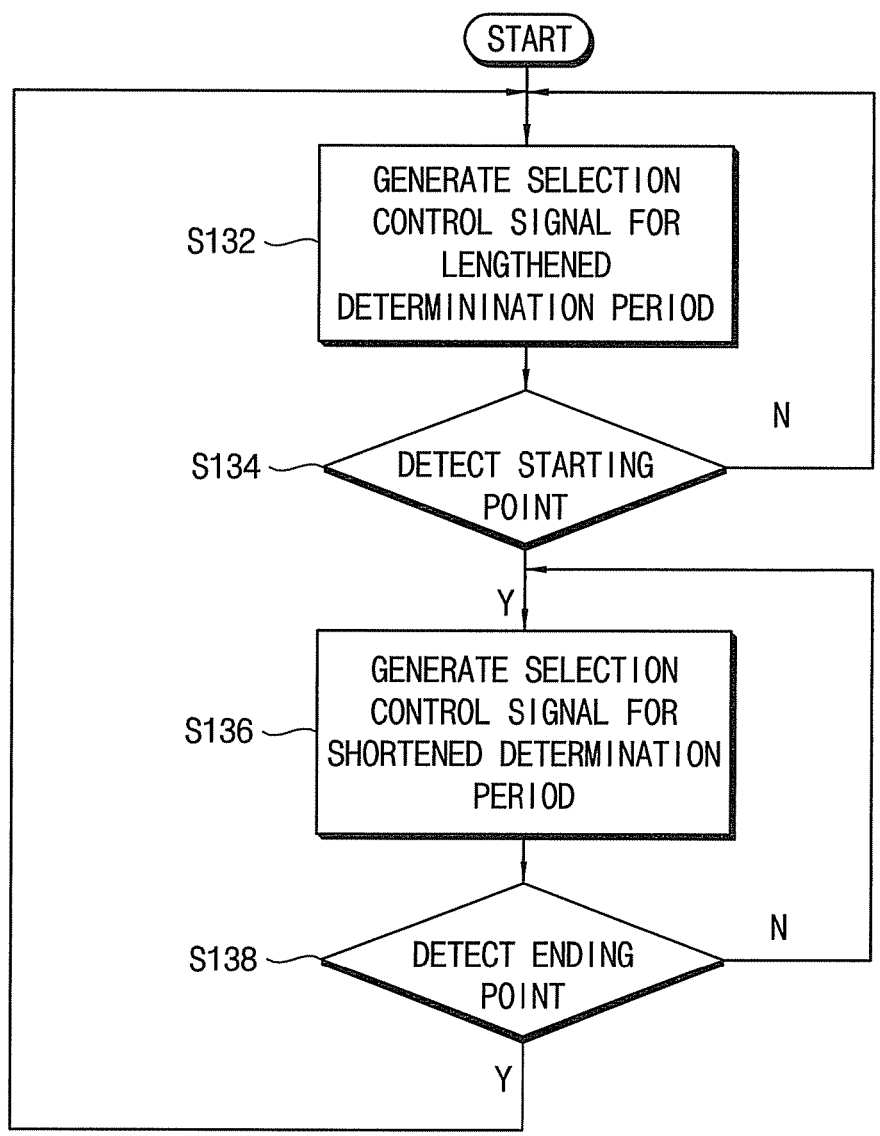
FIG. 14 is a flowchart for describing an example of automatic setting procedure of the determination period.

FIG. 14 is a flowchart for describing an example of automatic setting procedure of the determination period.

The detecting module 129 generates the selection control signal SC for selecting the lengthened determination period in an initial time to provide the selection control signal SC to the determination period selecting module 125 (step S132), and generates the selection control signal SC for selecting the shortened determination period when the starting point of the dynamic activity interval is detected (step 134) to provide the selection control signal SC to the determination period selecting module 125 (step S136). In step S136, the detecting program returns to step S132 when the ending point of the dynamic activity period is detected by the detecting module 129 (step S138). Therefore, the shortened determination period is selected in the dynamic activity interval in response to the detection of the dynamic activity interval, and the lengthened determination period is selected in the remaining intervals, that are the static activity intervals, excluding the dynamic activity interval.

Figure 15:
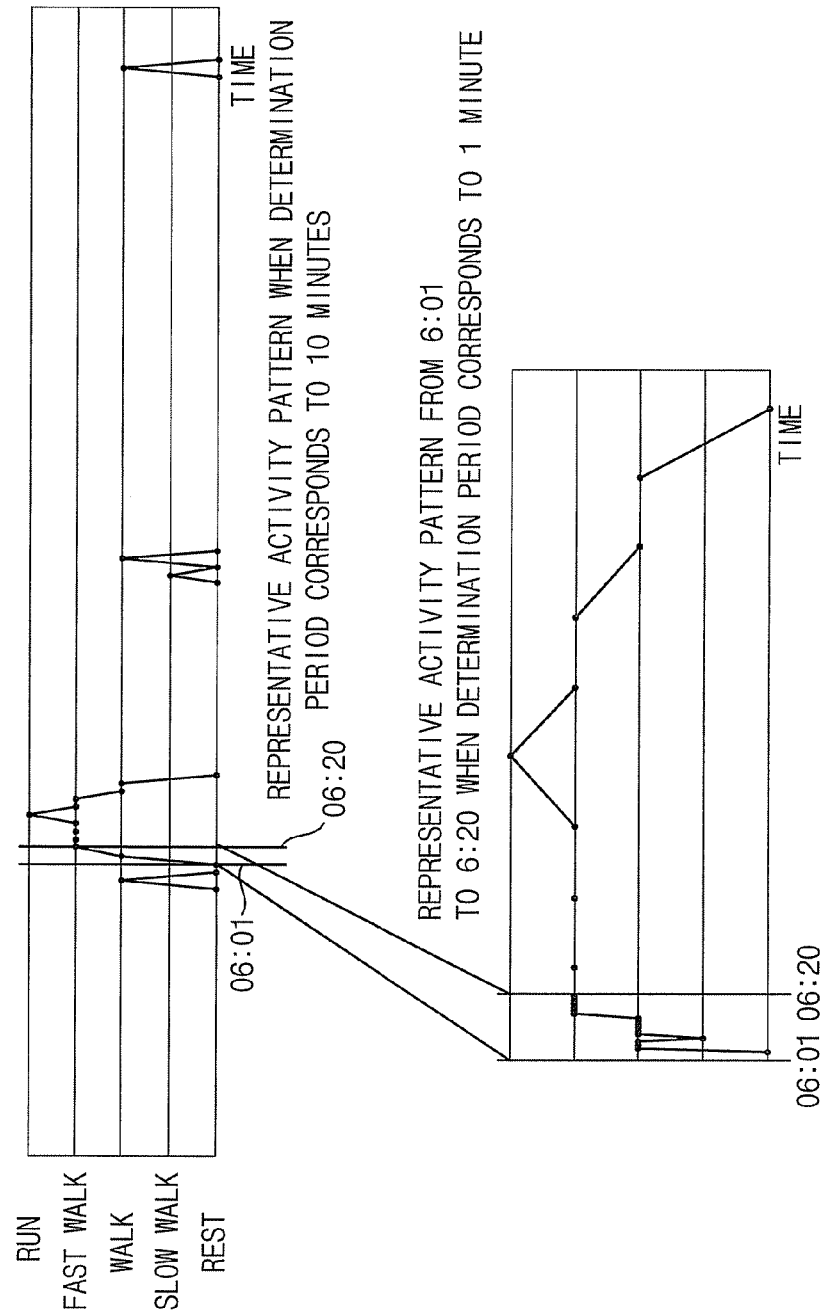
FIG. 15 is a diagram for comparing variations of the representative activity patterns between cases where the determination periods correspond to 10 minutes and 1 minute during 20 minutes from 6:01 to 6:20.

FIG. 15 is a diagram for comparing variations of the representative activity patterns between cases where the determination periods correspond to 10 minutes and 1 minute during 20 minutes from 6:01 to 6:20. When the determination period corresponds to 10 minutes, three kinds of the representative activity patterns may be determined. When the determination period corresponds to 1 minute, ten kinds of the representative activity patterns may be determined. When the determination period is lengthened, the amount of data may be reduced but the activity pattern may not be accurately analyzed. When the determination period is shortened, a state in which the user walks slowly after normal walking may be analyzed. However, the number of kinds of stored representative activity patterns is increased by 20.

The effective feedback for the present activity state may be provided to the user by applying the more shortened determination period to the dynamic activity intervals.

Figure 16:
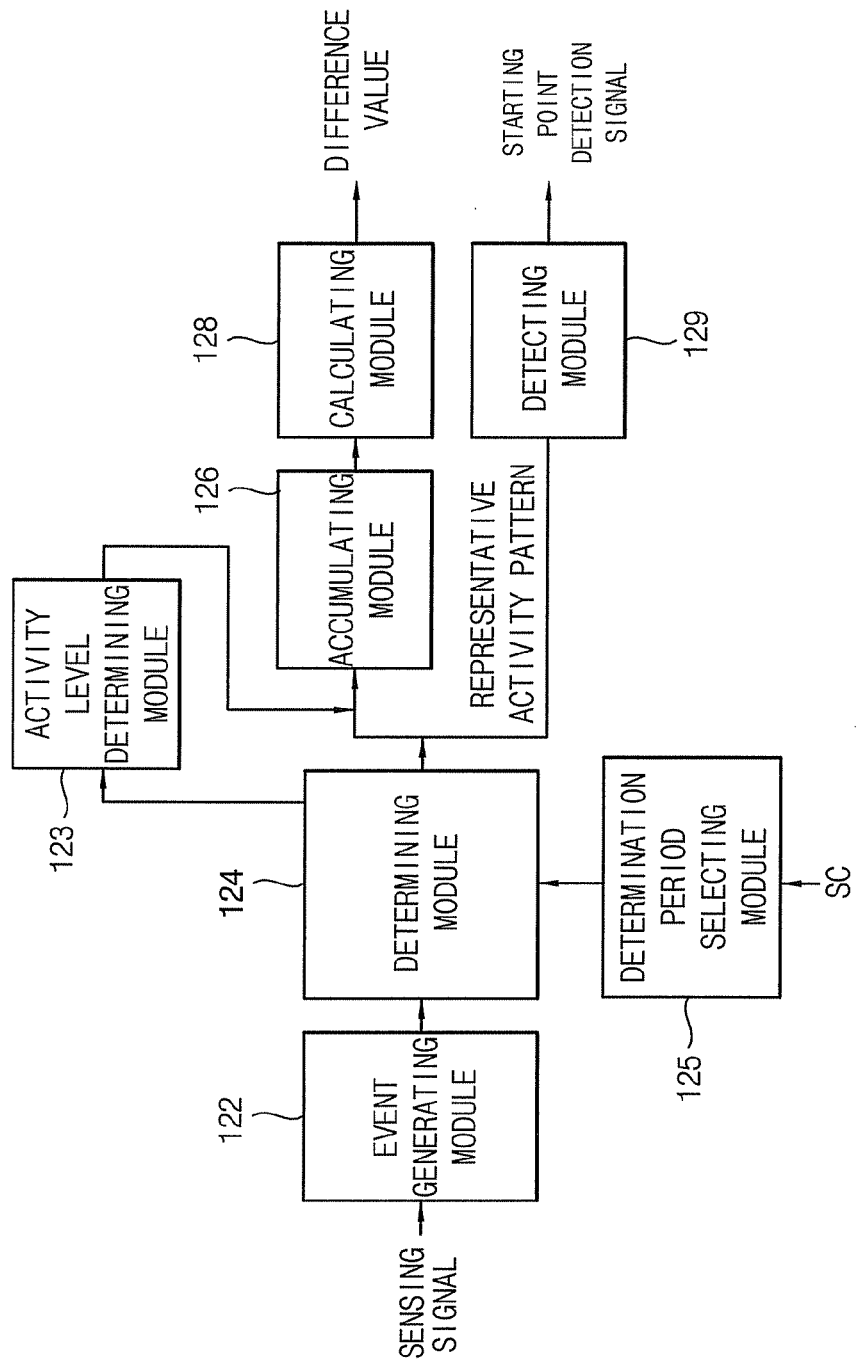
FIG. 16 is a detailed block diagram illustrating another example of the starting point detecting unit 120 in FIG. 1.

FIG. 16 is a detailed block diagram illustrating another example of the starting point detecting unit 120 in FIG. 1.

A starting point detecting unit 120-2 of FIG. 16 may further include an activity level determining module 123 compared to the starting point detecting unit 120. The same parts are represented with the same reference numerals, and thus a detailed description regarding the same parts will be omitted.

The activity level determining module 123 compares output waveforms of x-, y-, and z-axes and determines an activity level within four levels from 0 to 3 when an activity pattern is not classified into standardized activity patterns by the determining module 124.

Figure 17:
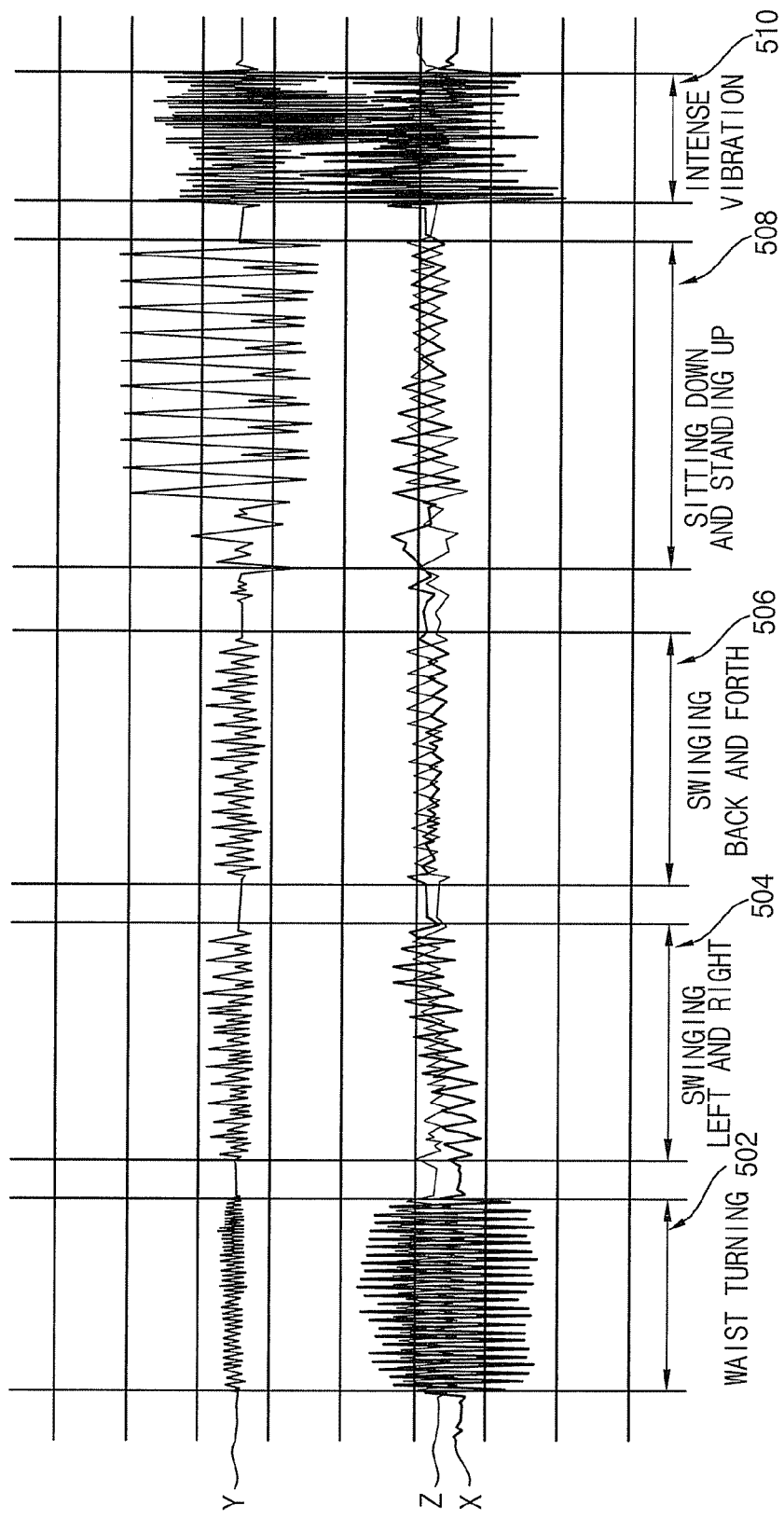
FIG. 17 is a diagram illustrating output waveforms of x-, y-, and z-axes obtained from the acceleration sensor when the activity pattern corresponds to a non-standardized activity pattern.

FIG. 17 is a diagram illustrating output waveforms of x-, y-, and z-axes obtained from the acceleration sensor when the activity pattern corresponds to a non-standardized activity pattern. With reference to FIG. 17, the waveform of y-axis remains almost static according to a vertical direction, and the waveforms of x- and z-axes rapidly fluctuate in waist turning 502. In swinging left and right 504, the waveform of the x-axis changes greater than the waveform of the z-axis. In swinging back and forth 506, the waveform of the z-axis changes greater than the waveform of the x-axis. In sitting down and standing up 508, the waveform of the y-axis greatly changes compared to the other waveforms, but a changing time is remarkably long compared to standard output waveforms. In an intense vibration 510, the waveforms of the x-, y- and z-axes quickly and greatly fluctuate.

Therefore, the activity state determined as the rest when the output waveforms of the x-, y-, and z-axes correspond to level 0, and then the activity level is determined to be level 0. When one of the output waveforms of the x-, y-, and z-axes is higher than level 0 and smaller than level 1, the activity level is determined to be level 1. For example, the swinging left and right or the swinging back and forth is determined to be level 1. When one of the output waveforms of the x-, y-, and z-axes is higher than level 1 and smaller than level 2, the activity level is determined to be level 2. For example, the waist turning is determined to be level 2. When one of the output waveforms of the x-, y-, and z-axes is higher than level 2, the activity level is determined to be level 3. For example, the sitting down and standing up or the intense vibration is determined to be level 3.

Figure 18:
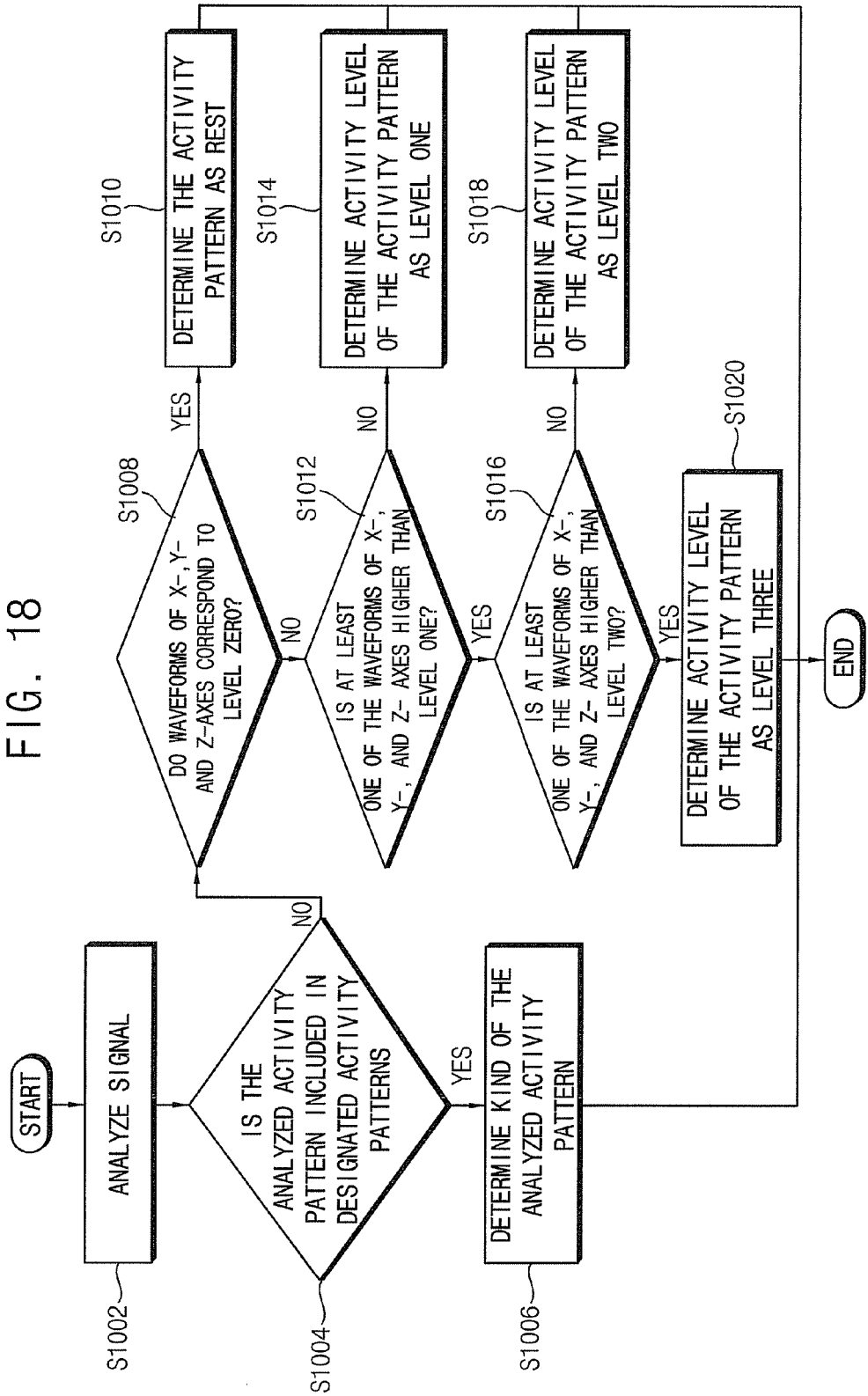
FIG. 18 is a flowchart for describing a sub-routine of step S110 in FIG. 13.

FIG. 18 is a flowchart for describing a sub-routine of step S110 in FIG. 13.

The determining module 124 analyzes the signal (step S1002), determines whether the analyzed activity pattern is classified into the designated activity patterns or not (step S1004), and determines the kind of the activity patterns when the analyzed activity pattern is included in the designated activity patterns (step S1006). In step S1004, the activity level determining module 123 determines whether all of the output waveforms of the x-, y-, and z-axes corresponds to level 0 when the analyzed activity pattern is not classified into the designated activity patterns (step S1008), and determines the activity level is level 0 when all of the output waveforms of the x-, y-, and z-axes corresponds to level 0 (step S1010). In step S1008, the activity level determining module 123 determines whether one of the output waveforms is greater than level 1 (step S1012), and determines the activity level is level 1 when neither of the output waveforms is greater than level 1 (step S1014). In step S1012, the activity level determining module 123 determines whether one of the output waveforms is greater than level 2 (step S1016), and determines the activity level is level 2 when neither of the output waveforms is greater than level 2 (step S1018). In step S1016, the activity level determining module 123 determines the activity level is level 3 when one of the output waveforms is greater than level 2 (step S1020).

Accurate activity intensities are difficult to sense when the exercise patterns or the activity patterns are determined by using the acceleration sensor, because humans have various kinds of activity patterns. Therefore, the activity patterns may be divided into 1,440 activity patterns when the activity patterns are determined in real life. However, approximately 20 to 25% of the total activity patterns are used when the standardized activity patterns are exclusively used, and thus accurate calorie calculation may be difficult because the remaining 75 to 80% is excluded.

Because the activity level is determined regarding the non-standardized activity patterns, the calculated calories may accurately obtained by weighting the determined activity level.

2. Example Embodiment 2

Online Server Supported Type—Applicable to Cellular Phones

Another example embodiment of the present invention is implemented to be supported by an online server different from the stand-alone apparatus. The online server supported apparatus may provide not only daily correction for the life pattern but also weekly, monthly, yearly, or lifelong correction for the life pattern. The online server supported apparatus corresponds to a network supported type apparatus which is able to provide consultations of health care professionals to the user through online.

Figure 19:
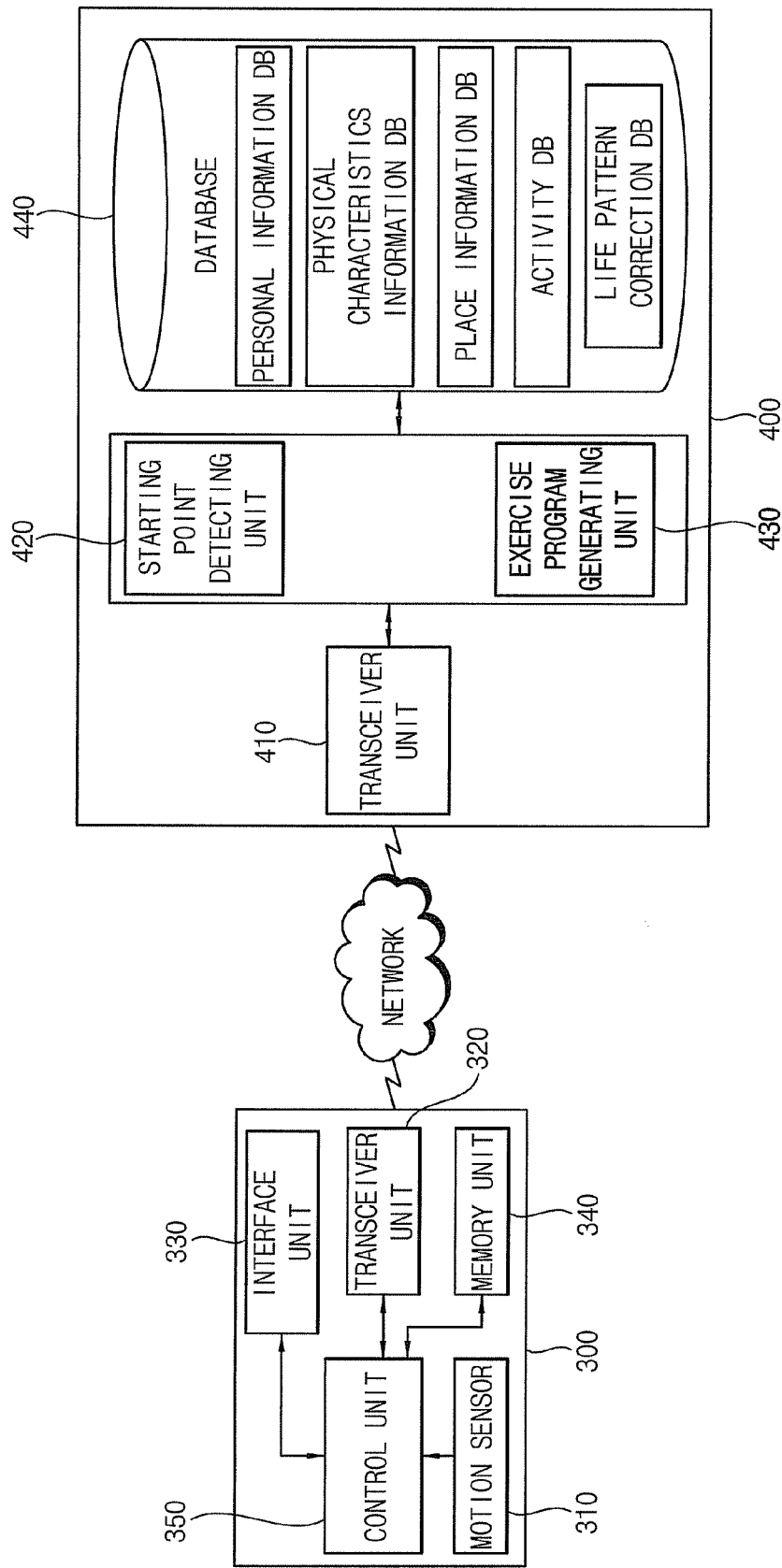
FIG. 19 is a block diagram illustrating a system for correcting life patterns implemented with the online server supported apparatus.

FIG. 19 is a block diagram illustrating a system for correcting life patterns implemented with the online server supported apparatus.

Referring to FIG. 19, a system is widely implemented with a handheld terminal 300 and a server 400. The handheld terminal 300 may include a motion sensor 310, a transceiver unit 320, a user interface unit 330, a memory unit 340, and a control unit 350. A mobile communication terminal configuration such as a cellular phone may be suitable for the handheld terminal 300.

The transceiver unit 320 transmits activity information sensed by the motion sensor 310 to the server 400, and receives starting point information of the dynamic activity intervals and exercise program information from the server 400 through the network. The control unit 350 outputs an exercise message corresponding to the exercise program information at the starting point received from the transceiver unit 320 through the user interface unit 330.

The handheld terminal 300 receives and outputs the related information from the server 400 instead of processing complex operations such as the detecting the starting point and generating the exercise program, and thus the handheld terminal 300 does not require a high-performance system.

The server 400 may include a transceiver unit 410, a starting point detecting unit 420, an exercise program generating unit 430, and a database 440. The transceiver unit 410 receives the activity information generated based on movement of the user who has the handheld terminal 300 periodically or in real time, and transmits the generated starting point information, determination period control information, and the exercise program information to the handheld terminal 300. The starting point detecting unit 420 detects the starting point of the dynamic activity interval based on the received activity information, and generates the determination period control information for setting the shortened determination period in the activity intervals at which the starting point is detected, different from the other activity intervals. The exercise program generating unit 430 generates the exercise program for filling a deficient amount of activity compared to the target value in the detected activity interval when the starting point is detected. The database 440 may include a personal information database, a physical characteristics information database, a place information database, an activity database, and a life pattern correction database. The place information database may include name of place, activity level (high, medium, low), duration of stay, travel time, travel method, and travel route.

3. Example Embodiment 3

Online Server Supported Type—Using Short Message Service

Another example embodiment of the present invention is implemented as the mobile device which is not implemented in the cellular phone similarly to the above-mentioned examples, but practically uses a short message service (SMS) to provide an exercise program for correcting life patterns.

FIG. 20 is a block diagram illustrating an example of online server supported system for correcting life patterns according to the present invention. The example embodiment is implemented in a mobile device 500, a server 600, and a cellular phone 700 by a fixed line and wireless.

The mobile device 500 may include a motion sensor 510, a transceiver unit 520, a user interface unit 530, a memory unit 540, and a control unit 550 similarly to the other example embodiments. However, the transceiver unit 520 may have a fixed-line access method connected to a desktop computer by a fixed-line local area network (LAN), a universal serial bus (USB), or an Institute of Electrical and Electronics Engineers (IEEE) 1394 and a wireless access method connected to an access pointer or the desktop computer by wireless LAN (WLAN), Bluetooth, or RFID, differently from the other example embodiments. Thus, another embodiment may be easily commercialized by combining with mobile devices such as a conventional pedometer.

The mobile device 500 generates the activity information for each determination period based on the movement of the user sensed by the motion sensor 510, stores the generated activity information to the memory unit 540, and periodically transmits the stored activity information to the server 600 through the transceiver unit 520 everyday. The user of the fixed-line access method uploads data after the mobile device is connected to the desktop computer, and then the uploaded data is uploaded to the server 600 through the Internet. In the wireless access method, the data stored in the mobile device 500 may be automatically uploaded to the server 600 when the mobile device 500 enters into the radio communication region. The daily activity information of the user may be transmitted to the server 600 when the user manually or automatically uploads the data using the personal computer connected to the Internet.

The server 600 may include an Internet connection unit 610, a starting point detecting unit 620, an exercise program generating unit 630, a database 640, and a mobile network connection unit 650. The server 600 analyzes the daily activity information received from the Internet connection unit 610, generates the determination period control information which sets the determination period shorter than the other activity intervals in the activity intervals in which the starting point is detected. The exercise program generating unit 630 generates the exercise program in response to the detected starting point, stores the starting point and the exercise program to the database 640, checks the time everyday, and transmits an SMS including the related exercise program and the determination period control information to the cellular phone 700 through the mobile communication connection unit 650 when the present time corresponds to the starting point detected the previous day. Therefore, the user may receive the SMS including the exercise program through the private cellular phone at the starting point of the dynamic activity interval corresponding to the same time detected the previous day. As long as the lifestyle of the user does not greatly change compared to the previous day, the user may receive the exercise program by the SMS at the starting point of the dynamic activity interval so that the user may maintain a dynamic life according to instructions from the exercise program.

INDUSTRIAL APPLICABILITY

An apparatus for correcting life patterns may reduce troublesome and bothersome inputting of data, and make inputting data easy by eliminating inputting of the data periodically or in real time so that a user may conveniently and adaptively use the apparatus. Further, the apparatus for correcting life patterns may be implemented without expensive components so that everyone may easily purchase and use the apparatus. Consequently, the apparatus may be widely spread and improve public health. In addition, the apparatus may contribute to analysis of studying habits of children, improving level of concentration, and correcting life patterns by direct instruction to increase movement when the user actually starts to move.

What is claimed is:

1. An apparatus for correcting life patterns in real time, comprising:
   a movement sensing unit configured to sense movements of a user for 24 hours a day;
   a starting point detecting unit configured to detect a starting point of a dynamic activity interval periodically or in real time based on the sensed movement information;
   an exercise program generating unit configured to generate an exercise program for filling a deficient amount of activity compared to a target value in the detected dynamic activity interval; and a user interface unit configured to provide the generated exercise program to the user at the starting point of the dynamic activity interval for increasing an exercise performance.

2. The apparatus for claim 1, wherein the starting point detecting unit comprises:

an event generating module configured to generate a corresponding event in response to the sensing signal from the movement sensing unit;

a unit activity pattern determining module configured to determine a unit activity pattern per unit time based on the generated event;

an accumulating module configured to accumulate consumed calories corresponding to the unit activity pattern;

a calculating module configured to calculate a difference value between the accumulation value and the target value; and a detecting module configured to compare an average amount of activity for every observation interval based on the determined unit activity pattern to detect the starting point in which the amount of activity rapidly changes.

3. The apparatus of claim 1, wherein the user interface unit configured to receive information of at least two activity places and information of duration for stay at least one of the at least the two activity places.

4. The apparatus of claim 3, wherein the exercise program generating unit configured to generate the exercise program based on the information of at least two activity places.

5. A server for correcting life patterns in real time, comprising:

a transceiver unit configured to receive activity information generated based on movement of a user, who possesses a handheld terminal, and to transmit generated starting point information and exercise program information to the handheld terminal;

a starting point detecting unit configured to detect a starting point of a dynamic activity interval of the user based on the received activity information; and an exercise program generating unit configured to generate an exercise program for filling a deficient amount of activity compared to a target value in the detected dynamic activity interval when the starting point is detected.

6. An apparatus for correcting life patterns in real time, comprising:

a mobile device configured to generate activity information in real time based on movements of a user, to store the activity information generated in real time, and to transmit the stored activity information to a server using a network;

the server being configured to detect a starting point of the dynamic activity interval based on the transmitted activity information, to generate an exercise program for filling a deficient amount of activity compared to a target value when the starting point is detected, and to transmit the generated exercise program to the mobile device of the user using a short message service (SMS) when a time of the next day corresponds to the starting point detected day; and the mobile device being configured to display the short message received from the server using a display unit.

7. An apparatus for daily correcting life patterns, comprising:

an activity sensing unit for sensing movements of a user in daily life;

a starting point detecting unit configured to detect a starting point of a dynamic activity interval for every first activity pattern determination period based on the sensed activity information, and to set an activity pattern determination period as a second activity pattern determination period during activity intervals where the starting point is detected, the second activity pattern determination period being different from the first activity pattern determination period;

an exercise program generating unit configured to generate an exercise program for filling a deficient amount of activity compared to a target value in the detected activity interval when the starting point is detected; and a user interface unit configured to provide the generated exercise program to the user.

8. The apparatus for claim 7, wherein the starting point detecting unit comprises:

an event generating module configured to generating a corresponding event in response to signals sensed from the activity sensing unit;

a determining module configured to determine a representative activity pattern for every first activity pattern determination period based on the generated event;

a determination period selecting module configured to set an activity pattern determination period as a second activity pattern determination period in an activity interval in which the starting point is detected, the second activity pattern determination period being different from the first activity pattern determination period;

an accumulating module configured to accumulate consumed calories corresponding to the representative activity pattern producing an accumulated value;

a calculating module configured to calculate a difference value between the accumulated value and the target value; and a detecting module configured to compare average amounts of activity for every observation period to detect the starting point at which the amount of activity rapidly changes.

9. A handheld terminal, comprising:

a movement sensing unit configured to generate activity information for every first activity pattern determination period based on movements of a user;

a memory unit for storing the activity information generated in real time;

a transceiver unit configured to transmit the stored activity information to a server, and to receive starting information of a dynamic activity interval, determination period control information, and exercise program information from the server using a network;

a user interface unit configured to output an exercise message based on the exercise program information; and a control unit configured to output the exercise message corresponding to the exercise program information at the starting point of the received dynamic activity interval, and to set an activity pattern determination period as a second activity pattern determination period in the dynamic activity interval in response to the determination period control information, the second activity pattern determination period being different from the first activity pattern determination period.

10. A server for correcting life patterns, comprising:

a transceiver unit configured to periodically receive activity information generated based on movements of a user who possesses a handheld terminal, and to transmit the generated starting point information, determination period control information, and exercise program information to the handheld terminal;

a starting point detecting unit configured to detect a starting point of the dynamic activity interval of the user based on the received activity information, and set an activity pattern determination period as a second activity pattern determination period in the activity interval in which the starting point is detected, the second activity pattern determination period being different from the first activity pattern determination period; and an exercise program generating unit configured to generate an exercise program for filling a deficient amount of activity compared to a target value in the detected activity intervals when the starting point is detected.

11. An apparatus for daily correcting of life patterns, comprising:

a movement sensing unit configured to sense movements of a user in daily life;

a starting point detecting unit configured to determine a respective standardized activity pattern and simultaneously determine a respective activity level of non-standardized activity patterns based on the sensed movement information, to detect starting points of a dynamic activity interval for a first activity pattern determination period based on the determined activity pattern and the activity level, and to set an activity pattern determination period as a second activity pattern determination period for an activity period in which the starting point is detected, the second activity pattern determination period being different from the first activity pattern determination period;

an exercise program generating unit configured to generate an exercise program for filling a deficient amount of activity compared to a target value in the detected activity interval when the starting point is detected; and a user interface unit configured to provide the generated exercise program information to the user.

12. The apparatus for claim 11, wherein the starting point detecting unit comprises:

an event generating module configured to generate a corresponding event in response to signals sensed from the movement sensing unit;

a determining module configured to determine a representative activity pattern for every first activity pattern determination period based on the generated event;

an activity level determining module for determining the activity level when the activity pattern is not detected by the determining module;

a determination period selecting module configured to set the activity pattern determination period as the second activity pattern determination period to provide to the determining module;

an accumulating module configured to accumulate consumed calories corresponding to the representative activity pattern and the activity level producing an accumulated value;

a calculating module configured to calculate a difference value between the accumulated value and the target value; and a detecting module configured to compare average amounts of activity based on the determined representative activity pattern for every activity pattern determination period, to detect the activity pattern determination period in which the amount of activity rapidly changes as a starting point.

* * * * *